United States Patent [19]

Schwierz et al.

[11] 4,297,582
[45] Oct. 27, 1981

[54] RADIATION DIAGNOSTIC DEVICE FOR GENERATING TOMOGRAPHIC IMAGES

[75] Inventors: Günter Schwierz; Rudolf Schittenhelm; Günter Schmitt, all of Erlangen; Edgar Tschunt, Rathsberg, all of Fed. Rep. of Germany

[73] Assignee: Siemens Aktiengesellschaft, Berlin & Munich, Fed. Rep. of Germany

[21] Appl. No.: 58,464

[22] Filed: Jul. 18, 1979

[30] Foreign Application Priority Data

Aug. 9, 1978 [DE] Fed. Rep. of Germany ....... 2834934

[51] Int. Cl.³ ............................................. G03B 41/16
[52] U.S. Cl. .................. 250/445 T; 250/360
[58] Field of Search ..................... 250/445 T, 360

[56] References Cited

U.S. PATENT DOCUMENTS

| | | | |
|---|---|---|---|
| 3,973,126 | 8/1976 | Ridington | 250/445 T |
| 3,983,399 | 9/1976 | Cox | 250/445 T |
| 4,139,776 | 2/1979 | Hillstrom | 250/445 T |

*Primary Examiner*—Craig E. Church
*Attorney, Agent, or Firm*—Hill, Van Santen, Steadman, Chiara & Simpson

[57] ABSTRACT

In the exemplary embodiments a layer is to be scanned which is generally parallel to the longitudinal axis of the patient support. For example, a radiation source and a radiation receiver may be rotated in an arc about a rotational axis which lies perpendicular to the longitudinal axis of the patient support to scan a layer area in such a way that the scanned layer within the exposure subject is traversed exclusively along beam paths each of which is crossed along its entire length in the subject by a multitude of other beam paths.

2 Claims, 8 Drawing Figures 4,297,582

RADIATION DIAGNOSTIC DEVICE FOR GENERATING TOMOGRAPHIC IMAGES

BACKGROUND OF THE INVENTION

The invention relates to a radiation diagnostic device for generating tomographic images of an exposure subject with a positioning table or patient support, with a measuring arrangement for irradiation of the exposure subject from various directions comprising a radiation source which emits radiation beams penetrating the layer to be investigated, the dimension of said radiation beams perpendicular to the layer plane being equal to the thickness of the layer, and a radiation receiver which supplies electrical output signals according to the measured radiation intensity, and with a computer connected to the radiation receiver for the calculation of the attenuation values of specific image points of the irradiated body layer from the output signals of the radiation receiver.

Radiation diagnostic devices of this type, so-called computer tomographs, are known in which the measurng arrangement is rotatable about an axis which lies in the longitudinal direction of the positioning table or patient support. In such apparatus, the x-ray source generates a fan-shaped x-ray beam which is received by a series of detectors which form the radiation receiver. If the measuring arrangement, whose x-ray source lies on the one side and whose radiation receiver lies on the other side of the positioning table is rotated around the exposure subject lying on the positioning table, then it is possible to calculate and visually reproduce the attenuation values of predetermined points of the layer of the exposure subject to be examined from output signals of the radiation receiver therby generated. With the known radiation diagnostic devices of the type initially cited, because of the position of the rotational axis of the measuring arrangement, it is only possible to generate tomographic images of layers of the exposure subject which lie transverse to the longitudinal axis of the exposure subject and transverse to the longitudinal direction of the positioning table.

SUMMARY OF THE INVENTION

The object of the invention is to design a computer tomograph in such manner that images of layers which lie in the longitudinal direction of the exposure subject, and, thus, of the positioning table can be generated with it.

This object is inventively achieved in that the rotational axis of the radiation beam intersects the longitudinal direction of the positioning table, in particular is arranged perpendicular thereto, in such manner that the scanned layer area in which the exposure subject lies is penetrated exclusively by rays in which each beam path is crossed over its entire length in the subject by many other beam paths and the angular range for the scanning rays seen from each subject point may be smaller than $\pi$ radians (180°). The invention proceeds on the basis that, with a layer scanning device of the type initially cited, a computational image reconstruction is possible when the scanned layer range of unkown ray attenuation is penetrated exclusively by rays in which each beam path is crossed over its entire length by many other beam paths, and that it is possible to meet this requirement by means of a suitable arrangement of the rotational axis of the measuring arrangement even in layer exposures in which the layer examined lies in the longitudinal direction of the patient positioning table.

A practical embodiment of the invention comprises an arrangement wherein the meauring arrangement is carried on a turntable for adjusting the position of the scanned layer, and the turntable is rotatble on a pedestal around a horizontal rotational axis as well as around the rotational axis lying perpendicular to the longitudinal direction of the postitioning table; and that the positioning table is seated on a second pedestal and can be adjusted in height. Given this embodiment, it is possible to examine layers of the exposure subject which lie in the longitudinal direction of the positioning table and have any desired angle to the positioning table as well as any desired interval from it.

A furher embodiment of the invention provides that the radiation source and the radiation receiver are fastened to a resective one of a pair of booms which encompass the positioning table, and that the radiation source has a beam shaping diaphragm allocated to it which is moved during a scanning process to progressively change the extent of a fanshaped beam in such manner that the marginal rays of the rays serving for the image calculation of the fan-shaped beam always extend tangential to two convex curves, preferably circular arcs, whose midpoints lie beyond the area covered by the scanning beam. Given this embodiment, extended longitudinal layers in the body to be examined can be represented. If the positioning table is rotataly arrranged around a vertical axis so that it can be brought into a position in which the rotational axis of the radiation beam lies parallel to the longitudinal axis of the positioning table or coincides with such longitudinal axis, then standard computer tomograms of layers which proceed perpendicularly through the exposure subject can also be produced with such a device.

In the following, the invention is described in greater detail on the basis of exemplary embodiments illustrated in the accompanying sheets of drawings; and other objects, features and advantages will be apparent from this detailed disclosure and from the appended claims.

DETAILED DESCRIPTION

Figure 1:
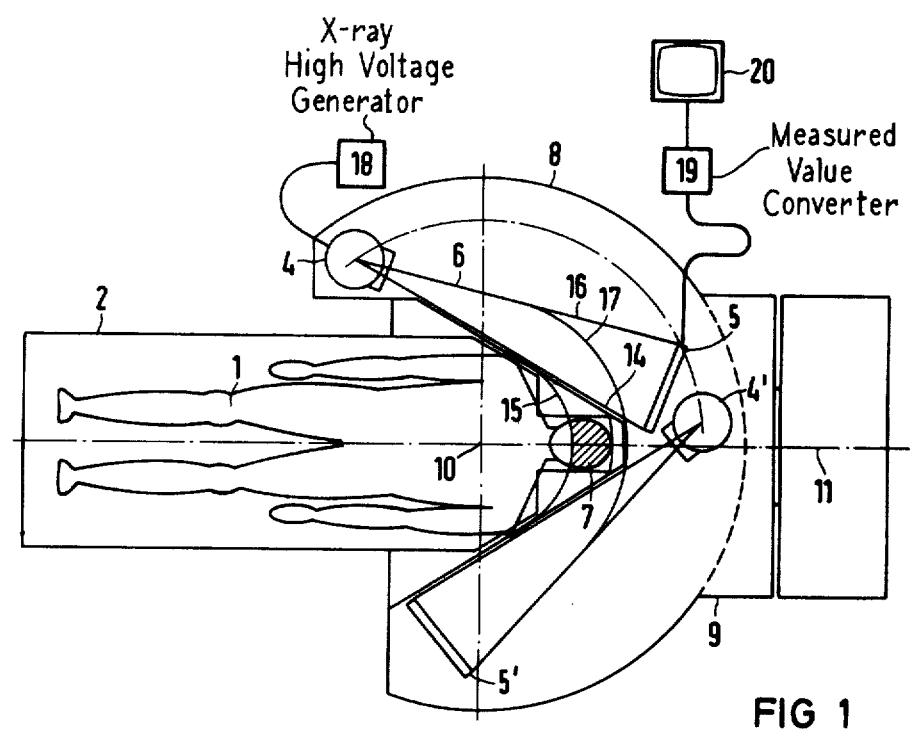
FIG. 1 is a diagrammatic top plan view of a radiation diagnostic device according to the invention.
Figure 2:
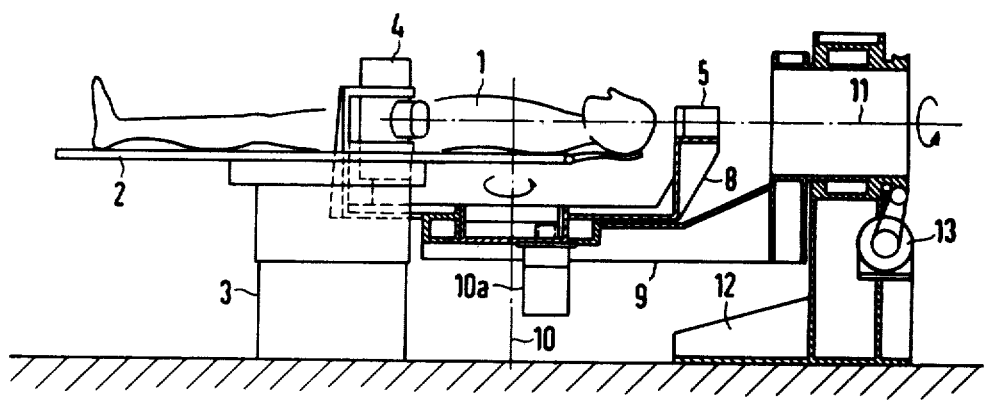
FIG. 2 is a side view of the radiation diagnostic device according to FIG. 1, with certain parts shown in vertical section.

A patient 1 lying on a positioning table or patient support 2 is illustrated in FIGS. 1 and 2. The positioning table 2 is mounted on a pedestal 3 so as to be adjustable in height and movable in the direction of its length. For examining the patient 1, namely the patient's head in the example, a measuring arrangement with an x-ray source 4 and a radiation receiver 5 is provided. The radiation receiver 5 consists of a series of individual detectors, for example in the order of more than 100 detectors, which are struck by a fan-shaped x-ray beam 6. In its dimension perpendicular to the examined layer 7 of the patient 1, the extent of the x-ray beam 6 is equal to the thickness of the layer. The measuring arrangement 4, 5 is fastened to a turntable 8 which is rotatable on a carrier 9 about an axis 10 by means of a motor 10a (FIG. 2). The carrier 9 is in turn connected with a footing 12 and rotatable around a horizontal axis 11. A motor 13 is provided for the rotation of the carrier 9 about horizontal axis 11.

FIG. 1 is intended to show that the measuring arrangement can be brought from an initial position with the x-ray source at 4 and the radiation receiver at 5 into a final position which is designated with 4' for the x-ray source and with 5' for the radition receiver by turning the turntable 8 about axis 10. During this rotation about axis 10, the one limiting ray path 14 of the x-ray beam 6 revolves on a circular arc 15 and the other limiting ray path 16 revolves on circular arc 17. The rotational axis 10 is located relative to the positioning table or patient support 2 in such a manner that the scanned layer of the patient's head (indicated by shading in FIG. 1), i.e. the layer area 7 of unkown beam attenuation to be examined, is exclusively penetrated along beam paths in the patient 1 each of which is crossed over its entire length, by a multitude of other beam paths during the rotation of the turntable 8. The angular range as seen from each subject point about which the x-ray source 4 is moved may be significantly smaller than $\pi$ radians; and preferably lies between $\pi$ and $\frac{1}{2}\pi$ radians. This requirement is met when the circular arc 17 lies beyond the head of the patient 1. During a scanning process, i.e. during the movement of the measuring arrangement from the initial position at 4, 5 into the final position designated by means of the symbols 4', 5', the x-ray source 4 which is fed by an x-ray generator 18 can be pulsed at periodic intervals. By so doing, a plurality of groups of output signals are obtained from the radiation receiver 5 corresponding to the number of pulses, such output signals being supplied to a computer or measured value converter 19. The computer 19, because of the fact that each beam path in the layer area 7 is crossed, along its entire length, by a plurality of other beam paths, is in a position to calculate the beam attenuation coefficients of predetermined array of points covering the layer area 7 from the output signals of the radiation receiver 5. Thereby, it is possible, by means of a corresponding control of a visual display 20, to reproduce an image of the layer area 7 after the scanning.

In the illustrated initial position of the turntable 8 with the measuring arrangement at 4, 5, FIG. 1, a layer, namely, the layer area 7, is scanned which lies parallel to the positioning table 2. By turning the turntable 8 about the horizontal axis 11, it is possible to also examine layers whose planes intersect with the plane of the positioning table 2. Because of the height adjustability of the positioning table 2, the examined layers can respectively have any desired height level.

In the exemplary embodiment, the examined layer area 7 lies between the two circular arcs 15 and 17, FIG. 1. It is important that the circular arc 17 proceed beyond the examined layer area, i.e. the scalp of th patient 1, for only in that case is the requirement met that each beam path in the layer of unkown beam attenuation is crossed, along its entire length, in the examination subject, by a multitude of other beam paths. In that case in which the circular arc 17 would proceed through the head of the patient, the layer area beyond the circular arc 17 would be penetrated by beam paths which have no intersection points in the above sense. In this case, therefore, no reconstruction of an image over the entire extent of the layer area 7 would be possible.

Figure 3:
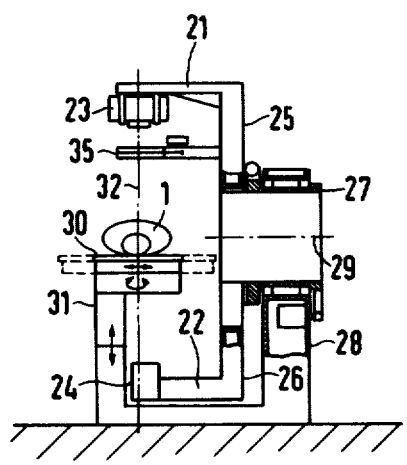
FIGS. 3 through 5 show various diagrammatic views of another embodiment of a radiation diagnostic device according to the invention.
Figure 4:
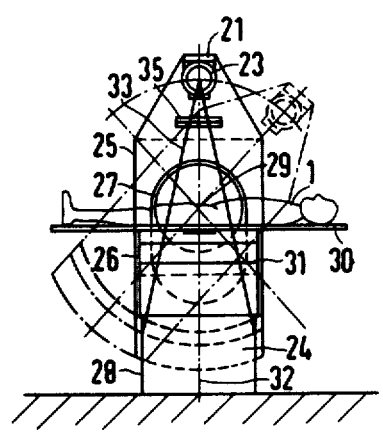
Figure 5:
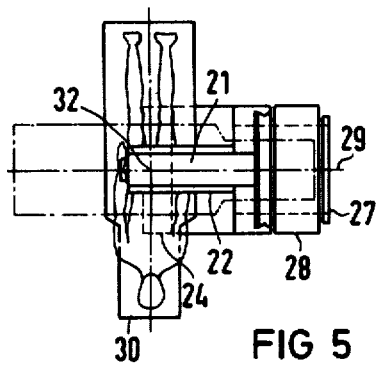

The device according to FIGS. 3 through 5 exhibits two booms 21 and 22. An x-ray tube 23 is fastened to the boom 21 and a radiation receiver 24 which likewise consists of a series of individual detectors is fastened to the boom 22. The booms 21 and 22, which encompass the positioning table 30, are connected by arms 25, 26 with a hollow shaft 27 which is rotatably journalled for rotation about an axis 29 on a pedestal 28. The positioning table or patient support 30 for the patient 1 is arranged displaceable in all directions on a carrier 31. The carrier 31 together with the positioning table 30 is height adjustable. Further, the positioning table 30 can be rotated with respect to the carrier 31 about a vertical axis 32.

Figure 6:
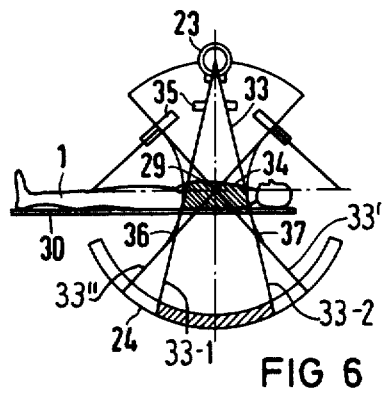
FIGS. 6 through 8 are schematic illustrations for explaining the manner of functioning of the device according to FIGS. 3 through 5.

In the illustrated position, any desired longitudinal layer of the patient 1 to be examined can be selected by means of a lateral displacement of the positioning table 30. In the case shown in FIG. 3, the selected longitudinal layer passes approximately through the axis of symmetry of the patient 1. If, for scanning the patient 1, the measuring arrangement 23, 24 is rotated around the axis 29 according to FIG. 6, then the x-ray beam 33, according to FIG. 6, scans the longitudinal layer 34 of the patient 1. A primary ray diaphragm 35 is adjusted during this scanning process in such manner that the marginal rays 33-1 and 33-2 of the fan-shaped ray beam 33 in the layer to be examined always proceed tangential to two arcs 36, 37 whose centers of curvature lie beyond the area to be scanned by the x-ray beam 33. In the two final positions 33' and 33'' of this x-ray beam illustrated in FIG. 6, the beam is constricted to a narrow beam by the ray diaphragm 35, whereas in the illustrated midposition the beam has its greatest width. By means of this adjustment of the ray diaphragm 35, one obtains, so to speak, a breathing x-ray beam, and the condition is met that the scanned layer area 34 be penetrated exclusively by beam paths in which each beam path is intersected, along its entire length in the subject, by a multitude of other beams paths.

Figure 7:
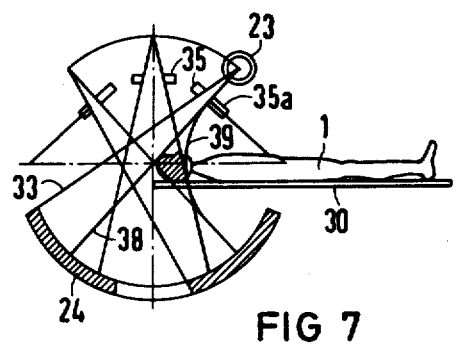

FIG. 7 shows a position in which the head of the patient is to be imaged. To this end, only the half of the ray diaphragm 35, namely the half 35a is adjusted so that the marginal beam 38 always proceeds tangential to one circular arc 39 which limits the examined layer in the head of the patient 1.

Figure 8:
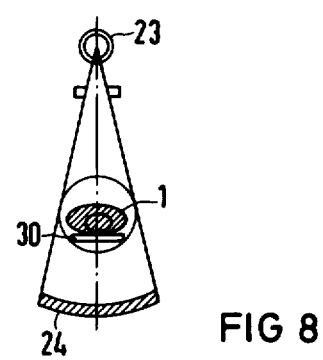

If the positioning table 30 is rotated by 90° from the position illustrated in FIGS. 3 through 7, then, in accordance with FIG. 8, a computer tomogram of a transverse layer of the patient 1 can be represented in a known manner.

For the sake of clarity, the x-ray generator as well as the computer and the visual display are not illustrated in FIGS. 3 through 8.

The exemplary embodiments according to FIGS. 1 and 2 are based on the theory that, for imaging a body layer with the assistance of a computer tomograph, projections from a scanning angular range which is smaller than 180° are sufficient when the scanning ensues in such manner that the center of rotation (in German the "Drehpunkt") of the x-ray beam lies beyond this x-ray beam. In the framework of the invention, it is not necessary in the example according to FIGS. 3 through 8 to also move the radiation receiver 24. It is possible to employ a radiation receiver of such an extent that it is always struck by x-rays and to use only those detectors of the radiation receiver which respectively receive the rays of the x-ray beam in each scanning position thereof. Further, it is conceivable to also displace the x-ray source linearly or to dispense with a mechanical movement of the x-ray tube when an x-ray tube is employed in which an electronic movement of the x-ray beam is possible in the sense of a rotation of its central beam.

In the framework of the invention, for imaging layers which lie oblique to the longitudinal direction of the patient, it is possible to arrange the rotational axis of the x-ray beam with an angle with respect to this longitudinal direction deviating from 90°, whereby it thereby also intersects this longitudinal direction, particularly the patient longitudinal axis.

It will be apparent that many modifications and variations may be effected without departing from the scope of the novel concepts and teachings of the present invention.

We claim as our invention:

1. A diagnostic device for generating layer images of an exposure subject, said device comprising
   (a) a patient support (2) providing a generally horizontal patient support surface at which a patient is supported so as to position a body layer to be examined in a longitudinally disposed scan plane generally parallel to the plane of said patient support surface and at a predetermined distance above the patient support surface less than the patient thickness,
   (b) a measuring arrangement for the irradiation of the body layer to be examined by means of x-rays to produce a series of scan projections with respective directional axes lying in said scan plane and each projection providing a multiplicity of beam paths in said scan plane and intersecting the body layer in a generally fan shaped beam configuration, said measuring arrangement including an x-ray radiation soruce (4) which emits x-ray radiation for providing said fan beam configuration in said scan plane with lateral extent corresponding to the extent of said body layer in said scan plane,
   (c) said measuring arrangement further including a radiation receiver (5) disposed in the plane of said fan shaped beam configuration and arranged to intercept the fan shaped beam configuration on the opposite side of the body layer from the radiation source during irradiation of the body layer for each scan projection in said scan plane, and to supply output signals corresponding to the measured radiation intensity for respective beam paths of the fan shaped beam configuration for each scan projection of the body layer,
   (d) a measured value converter (19) connected with the radiation receiver for calculating attenuation values for specific image points of the irradiated body layer from the output signals of the radiation receiver,
   (e) scanning means (8, 10a) coupled with said measuring arrangement and providing for movement thereof in said scan plane so as to irradiate said body layer along the respective directional axes in accordance with said series of scan projections during a scanning operation, and so that the body layer to be examined is scanned by being penetrated exclusively along beam paths of the fan shaped bean configuration each of which is crossed, along its entire length in the body layer, by a multitiude of other beam paths,
   (f) mounting means (9, 12) mounting said scanning means (8, 10a) such that the measuring arrangement moves along a path lying in the scan plane and such that the fan shaped beam configuration sweeps through an acruate region lying in the scan plane and extending from one side of the patient support to the other over an angular extent of substantially less than 360° to avoid irradiating a patient lying on the patient support except at the body layer, and
   (g) means comprising said scanning means and said mounting means for sweeping the fan beam configuration during a scanning operation in a scan plane lying a distance above the patient support surface less than the patient thickness such that a 360° movement of the measuring arrangement about the body layer, which is prevented by a patient on the patient support, is unnecessary to the production of a layer image of said body layer, said last-mentioned means directing the beam configuration obliquely relative to a radial line from the x-ray radiation source (4) to the center of curvature (10) of the arcuate region swept by the beam configuration such that the arcuate region swept by the beam configuration durng the scanning operation is essentially clear of the patient except at the body layer.

2. A diagnostic device for generating layer images of an exposure subject, said device comprising
   (a) a patient support (30) providing a generally horizontal patient support surface at which a patient is supported so as to position a body layer to be examined in a longitudinally disposed generally vertical scan plane which is disposed generally longitudinally of the patient support (30) and generally perpendicular to the plane of said patient support surface,
   (b) a measuring arrangement for the irradiation of the body layer to be examined to produce a series of scan projections with respective directional axes lying in said scan plane and each projection providing a multiplicity of beam paths in said scan plane and intersecting the body layer in a generally fan shaped beam configuration, said measuring arrangement including an x-ray radiation source (23) which emits x-ray radiation for providing said fan beam configuration in said scan plane with lateral extent corresponding to the extent of said body layer in said scan plane,
   (c) said measuring arrangement further including a radiation receiver (5) disposed in the plane of said fan shaped beam configuration and arranged to intercept the fan shaped beam configuration on the opposite side of the body layer from the radiation source during irradiation of the body layer for each scan projection in said scan plane, and to supply output signals corresponding to the measured radiation intensity for respective beam paths of the fan shaped beam configuration for each scan projection of the body layer,
   (d) scanning means (21, 22, 25, 26, 27) coupled with said measuring arrangement and providing for movement thereof in said scan plane so as to irradiate said body layer along the respective directional axes in accordance with said series of scan projections during a scanning operation, and so that the body layer to be examined is scanned by being penetrated exclusively along beam paths of the fan shaped beam configuration each of which is crossed, along its entire length in the body layer, by a multitude of other beam paths, (e) means (28, 31) positioning the scanning means (21, 22, 25, 26, 27) relative to the patient support (30) such that the measuring arrangement moves along a path lying in the scan plane and such that the radiation source (23) moves along an arcuate path having an angular extent of substantially less than 360° to avoid irradiating a patient lying on the patient support except of the body layer, and (f) means comprising said scanning means and said positioning means for orienting said radiation source such that a 360° movement of radiation source about the body layer, which is prevented by the patient support, is unnecessary to the production of a layer image of said body layer, and whereby such that the scan plane is directed generally longitudinally of the patient support to effectively scan longitudinal body layer of a patient on the patient support surface, (g) said scanning means limiting the path of movement of the radiation source (23) about the patient support (30) in the longitudinally directed scan plane to an angular extent such that interference between the radiation source (23) and the patient support (30) is avoided, (h) the patient support having a means laterally offset from the longitudinal center line of the patient support to provide for a relatively wide angular extent of movement of the measuring arrangement during a scanning operation.

* * * * *